United States Patent [19]

Ciccarelli

[11] 4,355,167
[45] Oct. 19, 1982

[54] TELOMERIC QUATERNARY SALT COMPOSITIONS

[75] Inventor: Roger N. Ciccarelli, Rochester, N.Y.

[73] Assignee: Xerox Corporation, Stamford, Conn.

[21] Appl. No.: 259,639

[22] Filed: May 1, 1981

[51] Int. Cl.³ .................... C07C 97/10; C07D 213/53
[52] U.S. Cl. .................................. 546/255; 430/106;
430/109; 430/110; 430/122; 525/359.1;
525/359.2; 525/359.3; 525/359.4; 525/359.5;
525/327.1; 526/263; 526/292.2; 546/267
[58] Field of Search ............... 546/255, 267, 341, 347;
560/81, 196; 260/501.12, 501.13; 564/288, 295;
525/336, 359.1–359.5; 526/263, 292.2; 430/106,
109, 110, 122

[56] References Cited

U.S. PATENT DOCUMENTS

| | | | |
|---|---|---|---|
| 2,484,430 | 10/1949 | Sprague et al. | 525/336 X |
| 2,487,829 | 11/1949 | Richards | 525/336 |
| 3,427,258 | 2/1969 | Trease | 252/500 |
| 3,786,058 | 1/1974 | Edwards | 546/255 X |
| 3,893,935 | 7/1975 | Jadwin et al. | 252/62.1 |
| 3,944,493 | 3/1976 | Jadwin et al. | 252/62.1 |
| 3,970,571 | 7/1976 | Olson et al. | 252/62.1 |
| 3,983,097 | 9/1976 | Okubo et al. | 525/336 X |
| 4,021,358 | 5/1977 | Tomono et al. | 252/62.1 |
| 4,070,186 | 1/1978 | Gibson et al. | 96/1 |
| 4,070,296 | 1/1978 | Gibson et al. | 252/62.1 |
| 4,079,014 | 3/1978 | Burness et al. | 252/62.1 |
| 4,139,459 | 2/1979 | Costin | 525/359.1 X |
| 4,139,718 | 2/1979 | Redmore et al. | 564/295 |
| 4,297,296 | 10/1981 | Baumann | 564/288 X |
| 4,298,672 | 11/1981 | Lu | 430/108 |
| 4,299,898 | 11/1981 | Williams et al. | 430/106 |

*Primary Examiner*—Richard Raymond
*Attorney, Agent, or Firm*—E. O. Palazzo

[57] ABSTRACT

This invention is directed to telomeric quaternary salt compositions of the formula $$[A_xB_y]z$$

wherein A is a segment selected from vinyl monomers, B is a quaternary salt segment, x and y are numbers representing mole fractions of A and B, the sum of x and y being equal to 1, and Z represents the degree of polymerization, wherein there results a telomeric quaternary salt having a number average molecular weight of from about 1,000 to about 10,000.

8 Claims, No Drawings

TELOMERIC QUATERNARY SALT COMPOSITIONS

BACKGROUND OF THE INVENTION

This invention is generally directed to novel telomeric quaternary salts, and more specifically, telomeric quaternary salts having a number average molecular weight of from about 1,000 to about 10,000. These salts are useful for example as charge enhancing additives for imparting positive charges to toner compositions, which toner compositions are employed together with carrier particles as developing materials in electrophotographic imaging systems. The toner and developer compositions containing the charge enhancing additive of the present invention are described and claimed in copending application identified, U.S. Ser. No. 259,789, filed on May 1, 1981, in the name of Roger N. Ciccarelli, the disclosure and examples of which are fully incorporated herein by reference.

While telomeric compositions, are known in the art, telomeric quaternary salts having a number average molecular weight of from about 1,000 to about 10,000 are not known, nor have they been isolated. Additionally, the use of such salts as toners and developers is not known in the art.

The electrophotographic process and more specifically, the xerographic process is well known, as documented in several prior art references. In these processes, an electrostatic latent image is developed by applying electroscopic particles or toner to the electrostatic latent image, using, for example, the cascade development method as described in U.S. Pat. No. 3,618,552, magnetic brush development as described in U.S. Pat. Nos. 2,874,063 and 3,251,706, or touchdown development as described in U.S. Pat. No. 3,166,432. In some instances, it may be desirable in such systems to produce a reverse copy of the original, thus, for example, it may be desired to produce a negative copy from a positive original, or a positive copy from a negative original.

In U.S. Pat. No. 3,893,935, there is disclosed the use of certain quaternary ammonium salts as charge control agents for electrostatic toner compositions. According to the disclosure of this patent, certain quaternary ammonium salts when incorporated into toner materials were found to provide a toner composition which exhibited relatively high uniform and stable net toner charge, when mixed with a suitable carrier vehicle. U.S. Pat. No. 4,079,014 contains a similar teaching with the exception that a different charge control agent is used, namely a diazo type compound.

Many of the described developers have a tendency to lose their positive charge over a period of time and in some instances, the charge enhancing additives employed are incompatible with the toner resin, thus making it difficult to uniformly disperse or dissolve such materials in the toner. Also, the charge control agents as described in U.S. Pat. No. 3,893,935 are soluble in water causing them to be leeched to the toner surface by moisture, thereby adversely affecting the machine environment in which they are used, and copy quality.

Some recently introduced commercial electrophotographic machines utilize organic photoconductors instead of inorganic photoconductors such as selenium, which photoconductors are charged negatively in comparison to selenium which is charged positively. Accordingly, toner materials containing a positive charge thereon are needed for causing the proper development of the images contained on the organic photoreceptor surface. While the prior art describes the use of charge control agents for imparting a positive charge to the toner resin, there continues to be a need for new materials which provide a high positive charging intensity to the toner resin, which intensity is maintained at relatively the same level over an extended period of time. Some charge control agents while they initially impart a positive charge to the toner resin, may not be capable of maintaining that charge over a long period of time, and further such charge control agents may be incompatible with the development system thereby adversely affecting the quality of the images developed. Also some of the prior art charge control agents are incompatible with the toner resin material which adversely affects the charge inducing properties of the charge control agent.

Accordingly, there is a need for new telomeric quaternary ammonium salts, which salts are of a specific molecular weight, thus enabling them to possess specific properties, particularly when such salts are used as charge enhancing additives for toner and developer compositions. Such toners and developer compositions can be used in reversal imaging systems particularly those systems wherein positively charged toner materials are required, which positive charge is substantially high and can be maintained over a long period of time, thus allowing the production of high quality images in an electrophotographic system.

SUMMARY OF THE INVENTION

It is an object of the present invention to provide novel telomeric quaternary salts.

It is a further object of the present invention to provide novel telomeric quaternary salts of a number average molecular weight of from about 1,000 to about 10,000, which salts are useful as charge enhancing additives in toners and developer compositions.

A further object of the present invention is the provision of novel telomeric quaternary salts which when used in toner and developer compositions as charge enhancing additives, will not migrate or move from the toner particles to the carrier particles, thereby effecting the charge relationship involved, and the final charge contained on the toner resin, and further, which charge enhancing additives are compatible with the toner resin, while at the same time having controlled dispersibility, that is, the degree of solubility/dispersibility is selected and controlled as desired.

These and other objects of the present invention are accomplished providing novel telomeric quaternary salts of the formula $$[A_xB_y]Z$$

wherein A is a segment selected from vinyl monomers, B is a quaternary salt segment, x and y are numbers representing mole fractions of A and B, the sum of x and y being equal to 1, and Z represents the degree of polymerization, which polymerization is controlled and adjusted, wherein there results telomeric quaternary salts having a number average molecular weight of from about 1,000 to about 10,000. The anion associated with the quaternary salt segment B can be any suitable anion, examples of which are Br⁻, Cl⁻,

$CH_3SO_4^-$, $NO_3^-$, $H_2PO_4^-$, $CH_3SO_4^-$, $CH_3SO_3^-$,

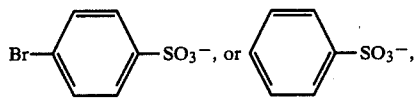

or $OH^-$. Also included within the scope of the present invention, and within the definition of quaternary salts are the mineral acid salts, and organic acid salts of amines, such as the HCl, HBr, HI, $NHO_3$, $H_2SO_4$, etc. salts.

A may represent any segment that is compatible with a toner resin, however, illustrative examples of A include conventional vinyl monomers, and in particular, styrene and substituted styrenes, and acrylates such as alkylacrylates including methacrylates.

Illustrative examples of the B segment include for example, quaternary salts prepared from amine containing vinyl monomers, such as 2-vinylpyridine, 3-vinylpyridine, 4-vinylpyridine, substituted vinyl pyridines, amine acrylates and methacrylates such as mono and dialkylaminoethylmethacrylates, an example of which is dimethylaminoethylmethacrylate and the like.

The letters x and y represent numbers with the provision that the sum of x plus y must be equal to 1. Thus, y may represent the number 0.9 and x may represent the number 0.1 or x may represent the number 0.9 and y may represent a number 0.1. The ratio of x to y can for example by 0.75 to 0.25, 0.96 to 0.04, 0.0 to 1.0, 0.90 to 0.10, 0.98 to 0.02, and the like. In one embodiment of the present invention x represents the number 0.9 and y represents the number 0.1 the sum of x plus y being equal to 1.

The telomeric quaternary salts of the present invention are prepared by reacting the appropriate telomeric amines with certain quaternizing materials such as alkyl halides. Accordingly, there can be reacted from about 1 mole of a telomeric amine, such as styrene/4-vinyl pyridine, with about 1 to 25 moles of an alkyl halide, such as butyl chloride or butyl bromide, the reaction being accomplished at a temperature of from about 20 degrees centigrade to about 120 degrees centigrade, followed by separating the desired product by known methods including filtering and washing. In order to obtain a telomeric quaternary salt of a number average molecular weight of from about 1,000 to about 10,000 the degree of polymerization Z is controlled by for example, terminating the polymerization reaction utilizing a chain transfer agent, as described herein. Also the ratio of X to Y is obtained by adjusting the monomer feed ratios and the reactivity ratios of the A and B segments described herein, thus reacting about 0.90 moles of styrene, with about 0.10 moles of vinyl pyridine, results in a ratio of X to Y of 0.90:0.10. The type of reactions involved are described in Polymer Handbook, 2nd Edition, J. Brandrup and E. H. Immergut, John Wiley & Sons, New York, 1975, pages 1057, and Free Radical Telomerization, C. M. Starks, Academic Press, New York, 1974, the disclosure of which is totally incorporated hereinby reference.

The novel telomeric amines employed in the reaction are prepared in accordance with the disclosure of copending application U.S. Ser. No. 259,789, filed on May 1, 1981, in the name of Roger N. Ciccarelli, the subject matter of which is totally incorporated herein by reference. Thus for example the telomeric amines are prepared by reacting an appropriate monomer such as styrene, with a vinyl pyridine, in the presence of a chain transfer agent.

The chain transfer agent employed in the preparation of the quaternary salts of the present invention is selected in accordance with the following equation:

$$\frac{[TX]}{[A]} = \frac{1}{T} \frac{[rBX^2 + 2X + rA]}{[r_B C_{BT} X + r_A C_{AT}]}$$

where [TX]=chain transfer agent concentration in moles.

wherein [A] and [B]=monomer concentration in moles.

where T=average degree of polymerization where X=[B]/[A]

where $r_A$ and $r_B$ are monomer reactivity ratios.

where $C_{AT}$ and $C_{BT}$ are the chain transfer constants.

Among suitable chain transfer agents are carbon tetrachloride, iso-butyraldehyde, n-butyraldehyde, and the like, with n-butyraldehyde being preferred.

Also, Z, the degree of polymerization can be controlled by proper choice and concentration of a suitable initiator such as benzoylperoxide and azo-bis-isobutyronitrile to produce oligomers having the desired molecular weight.

Ilustrative specific materials embraced by the above-identified formula include quaternary salts, anhydrous, hydrated, or partially hydrated, prepared from telomeric and oligomeric amine copolymers such as, styrene/4-vinylpyridine, styrene/2-vinylpyridine, styrene/3-vinylpyridine, styrene/dimethylaminoethylmethacrylate, styrene/t-butylaminoethylmethacrylate, n-butylmethacrylate/4-vinylpyridine, n-butylmethacrylate/2-vinylpyridine, n-butylmethacrylate/3-vinylpyridine, n-butylmethacrylate/dimethylaminoethylmethacrylate, n-butylmethacrylate/t-butylaminoethylmethacrylate, and the like. There may be substituted for the styrene and butyl acrylate segments, alkyl and halo substituted styrenes, acrylates, alkyl substituted methacrylates, while alkyl substituted vinyl pyridines may be substituted for the vinyl pyridines. Typical alkyl substituents include methyl, ethyl, propyl, butyl, pentyl, hexyl, and the like. Illustrative examples of telomeric quaternary salts prepared from the above amine copolymers include styrene/vinyl-N-alkyl pyridinium halides, styrene/2-vinyl-N-ethyl pyridinium chloride monohydrate, styrene/2-vinyl-N-butyl pyridinium chloride monohydrate, styrene/3-vinyl-N-butyl pyridinium chloride monohydrate, styrene/4-vinyl-N-butyl pyridinium chloride, styrene/2-vinyl-N-butyl pyridinium monohydrate, styrene/3-vinyl-N-butyl pyridinium bromide monohydrate, styrene/4-vinyl-N-butyl pyridinium bromide monohydrate, and the like.

When employed as a charge enhancing additive in a developer composition, the amount of telomeric quaternary salts added to the toner resin ranges from about 0.1 percent by weight to about 50 percent by weight and preferably from about 0.1 percent by weight to about 20 percent by weight. The salts can be blended into the system or coated onto the pigment or colorant such as carbon black which is part of the developing composition.

While any suitable resin may be mixed with the salts of the present invention, for preparing toner compositions, typical of such resins are polyamides, epoxies, polyurethanes, vinyl resins and polyester especially those prepared from dicarboxylic acids and diols comprising diphenols. Any suitable vinyl resin may be employed in the toners of the present system, including homopolymers or copolymers of two or more vinyl monomers. Typical of such vinyl monomeric units include: styrene, p-chlorostyrene, vinyl naphthalene, ethylenically unsaturated mono-olefins such as ethylene, propylene, butylene, isobutylene and the like; vinyl halides such as vinyl chloride, vinyl bromide, vinyl fluoride, vinyl esters such as vinyl acetate, vinyl propionate, vinyl benzoate, vinyl butyrate and the like; esters of ethylinic aliphatic monocarboxylic acids such as methyl acrylate, ethyl acrylate, n-butylacrylate, isobutyl acrylate, dodecyl acrylate, n-octyl acrylate, 2-chloroethyl acrylate, phenyl acrylate, methylalpha-chloroacrylate, methyl methacrylate, ethyl methacrylate, butyl methacrylate and the like; acrylonitrile, methacrylonitrile, acrylamide, vinyl ethers such as vinyl methyl ether, vinyl isobutyl ether, vinyl ethyl ether, and the like; vinyl ketones such as vinyl methyl ketone, vinyl hexyl ketone, methyl isopropenyl ketone and the like; vinylidene halides such as vinylidene chloride, vinylidene chlorofluoride and the like; and N-vinyl indole, N-vinyl pyrrolidone and the like; and mixtures thereof. Other resins include polyester compositions as described in U.S. Pat. Nos. 3,655,374 and 3,590,000.

Any suitable pigment or dye may be employed as the colorant for the toner particles, such materials being well known and including for example, carbon black, nigrosine dye, aniline blue, calco oil blue, chrome yellow, ultramarine blue, DuPont oil red, methylene blue chloride, phthalocyanine blue and mixtures thereof. The pigment or dye should be present in the toner in sufficient quantity to render it highly colored, so that it will form a clearly visible image on the recording member. For example, where conventional xerographic copies of documents are desired, the toner may comprise a black pigment, such as carbon black, or a black dye such as Amaplast black dye available from the National Aniline Products, Inc. Preferably, the pigment is employed in amounts from about 3% to about 20% by weight based on the total weight of toner, however, if the colorant employed is a dye, substantially smaller quantities may be used.

Any suitable carrier material can be employed, together with the toner particles containing the salts of the present invention, providing such carrier particles are capable of triboelectrically obtaining a charge of opposite polarity to that of the toner particles. Examples of suitable carrier materials include sodium chloride, ammonium chloride, potassium chloride, Rochelle salt, sodium nitrate, aluminum nitrate, potassium chlorate, granular zircon, granular silicon, methylmethacrylate, glass, steel, nickel, iron ferrites, silicon dioxide and the like, with metallic carriers especially magnetic carriers being preferred. The carriers can be used with or without a coating. The coatings generally contain fluorinated polymers such as polyvinyl fluoride resins, but other resins especially those which charge negatively, such as polystyrene, halogen containing ethylenes and the like can be used. Many of the typical carriers can be used as described in U.S. Pat. Nos. 2,618,441; 2,638,522; 3,618,522; 3,591,503; 3,533,835; and 3,526,533. Also nickel berry carriers as described in U.S. Pat. Nos. 3,847,604 and 3,767,598 can be employed, these carriers being nodular carrier beads of nickel characterized by a surface of reoccurring recesses and protrusions providing particles with a relatively large external area. The diameter of the coated carrier particle is from about 50 to about 100 microns, thus allowing the carrier to possess sufficient density and inertia to avoid adherence to the electrostatic images during the development process.

The carrier particles may be employed with the toner composition in any suitable combination, however, best results are obtained when about 1 part per toner is used, to about 10 to about 200 parts by weight of carrier.

Developing compositions, containing the telomeric salts of the present invention may be used to develop electrostatic latent images on any suitable electrostatic surface capable of retaining charge, including conventional photoconductors, however, such developing compositions are best utilized in systems wherein a negative charge resides on the photoreceptor, and this usually occurs with organic photoreceptors, illustrative examples of such photoreceptors being polyvinyl carbazole, 4-dimethylaminobenzylidene, benzhydrazide; 2-benzylidene-aminocarbazole, (2-nitro-benzylidene)-p-bromoaniline; 2,4-diphenyl-quinazoline; 1,2,4-triazine; 1,5-diphenyl-3-methyl pyrazoline 2-(4'-dimethyl-amino phenyl)-benzoxazole; phthalocyanines and mixtures thereof.

Toner and developer compositions containing the telomeric quaternary enhancing salt of the present invention also rapidly charge new uncharged toner, which is added as replenishment material to a developer composition. This is known as rapid admix charging. By admix charging is meant providing the appropriate charges, for example, in the present invention, positive charges, at a rapid rate to new uncharged replenishment toner being added to the toner which already contains charges thereon. As is customary in xerographic imaging systems, new toner, that is, toner resin plus colorant, must be added to the system as toner is being consumed for the development of images. In the past, the new uncharged toner being added did not obtain appropriate charge until a signficant period of time had elapsed, for example, after 10 to 15 minutes. This adversely effected the developer composition and thus good high quality images would not result until a new uncharged toner had acquired the appropriate electrical charges. In some instances, no images whatsoever could be developed until the uncharged toner was mixed with the charged toner and the machine system being used, which usually involved 10 to 15 minutes mixing time. With the telomeric quaternary salt of the present invention, the rate at which the uncharged toner acquires charge, which is positive charge, is substantially less than 10 minutes. Typically, the uncharged toner becomes suitably charged within from about one minute to about five minutes, and preferably less than three minutes. Such rapid admix charging allows the developer system to become more stable over a shorter period of time as compared to prior art systems, therefore, better quality images are obtained with no background. This was a significant finding that was not appreciated by the prior art.

The following examples are being supplied to further define the species of the present invention, it being noted that these examples are intended to illustrate and not limit the scope of the present invention. Parts and percentages are by weight unless otherwise indicated, and Z represents the degree of polymerization, wherein there results the materials of the molecular weights indicated.

EXAMPLE I

There was prepared the telomer styrene/4-vinylpyridine by heating together a mixture of 83.3 grams of purified styrene monomer, 21.0 grams of purified 4-vinylpyridine monomer, 243.5 grams of n-butyraldehyde, and 2.1 grams of 2,2'-azo-bis-isobutyronitrile (AIBN) for 21 hours at 75° C. under an argon blanket. The monomers were purified before use by treatment with Basic Alumina Woelm B. The telomeric amine was isolated by precipitation into a large excess of isomeric hexanes (Fisher H-291) (boiling range 65°–68° C.). The telomer was then purified by dissolving in chloroform, followed by washing with dilute aqueous sodium hydroxide solution, drying over Linde Molecular Sieve No. 4A, and then precipitated by adding the telomer to a large excess of isomeric hexanes. The resulting product was then vacuum dried in an oven. There was isolated in a 70 percent yield a styrene/4-vinylpyridine telomer of the formula

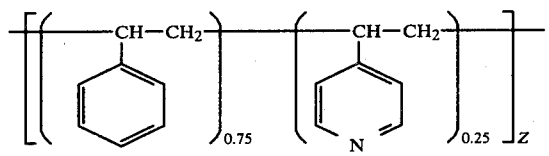

This telomer had a number average molecular weight of 2,500, and a weight average molecular weight of 5,100. The styrene mole fraction 0.75, and the 4-vinylpyridine mole fraction 0.25 were experimentally verified by elemental carbon/hydrogen/nitrogen analysis. Found: 88.78% C, 8.01% H, 3.35% N; Calc: 89.15% C, 7.50% H, 3.36% N.

EXAMPLE II

There was prepared the quaternary salt telomer, styrene/4-vinyl-N-butylpyridinium bromide monohydrate, by heating together a mixture of 125 grams of the styrene/4-vinylpyridine telomer prepared in Example I, 825 grams of n-butylbromide (Eastman #51), and 1,400 grams of acetonitrile (Baker #3-9255) for 120 hours at 75° C. under an argon blanket. The solution was filtered and then vacuum stripped to dryness on a Buchi-Rotavapor-R rotary evaporator. Vacuum conditions are slowly increased from 25° C./80 mm. to a final 70° C./50 mm. Hg pressure. The product is dried in a vacuum oven at 60° C. for 20 hours. There was isolated in 96 percent yield a styrene/4-vinyl-N-butylpyridinium bromide monohydrate telomer of the formula:

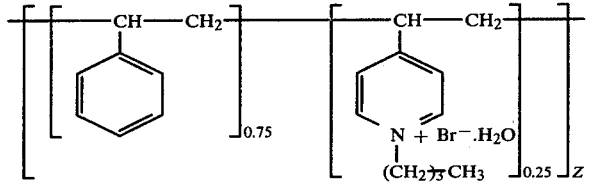

This material had a number average molecular weight of 3,400 and a weight average molecular weight of 7,000. The styrene mole fraction 0.75 and the 4-vinyl-N-butylpyridinium bromide monohydrate mole fraction 0.25 were experimentally verified by elemental carbon/hydrogen/nitrogen/bromine/oxygen analysis, and Karl Fischer water analysis. Found: 73.40% C, 7.42% H, 2.52% N, 13.76% Br, 2.85% O, 3.25% $H_2O$; Calc: 73.40% C, 7.41% H, 2.45% N, 13.95% Br, 2.79% O, 3.15% $H_2O$.

EXAMPLE III

The procedure of Example I was repeated with the exception that the ratio of styrene monomer to 4-vinylpyridine monomer was adjusted in order to prepare a styrene/4-vinylpyridine telomer having a styrene mole fraction of 0.96 and a 4-vinylpyridine mole fraction of 0.04.

EXAMPLE IV

The procedure of Example I was repeated with the exception 4-vinylpyridine monomer was polymerized in the absence of styrene monomer to prepare a 4-vinylpyridine telomer having 4-vinylpyridine mole fraction of 1.0.

EXAMPLE V

The procedure of Example II was repeated with the exception that the 4-vinylpyridine telomer from Example IV was quaternized with n-butylbromide. There was isolated the quaternary salt telomer, 4-vinyl-N-butylpyridinium bromide monohydrate of the formula

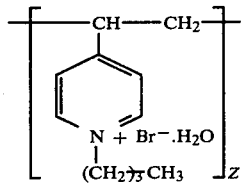

This material had an average number molecular weight of about 3,200.

EXAMPLE VI

The procedure of Examples I and II was repeated with the exception that there was prepared the telomers styrene/2-vinylpyridine, and styrene/3-vinylpyridine, and these telomers were reacted with n-butyl bromide in accordance with the procedure of Example II, whereby there resulted the quaternary salt telomers styrene/2-vinyl-N-butylpyridinium bromide monohydrate, and styrene-3-vinyl-N-butylpyridinium bromide monohydrate. In a like manner, the corresponding chloride quaternary salts were prepared by reacting the respective telomers with n-butylchloride in a pressure reactor.

EXAMPLE VII

A toner composition was prepared by melt blending, followed by mechanical attrition, 3.2 parts of the styrene/4-vinyl-N-butylpyridinium bromide monohydrate quaternary salt telomer of Example II with 6 parts Regal 330 carbon black and 90.8 parts of a styrene/n-butylmethacrylate resin, 65 percent by weight of styrene, 35 percent by weight of n-butylmethacrylate. The reslting blend was attrited and classified resulting in toner particles. Two and one half parts, (2.5 parts) of this toner, and 97.5 parts of a carrier comprised of 0.175 percent Kynar 201, vinylidene fluoride resin available from Penwalt Corporation, coated on atomized steel carrier, were blended into a developer composition. The developer composition was roll milled, and after 10 minutes of roll milling the triboelectric charge on the toner was measured and found to be +63 uc/gram (microcoulombs per gram). This developer was tested in an imaging fixture using the photoreceptor polyvinylcarbazole charged negatively and good quality prints of excellent resolution were obtained.

EXAMPLE VIII

The procedure of Example VII was repeated with the exception that the toner composition was comprised of 3.2 parts of the quaternary salt of Example II, 8 parts Regal 330 carbon black, and 88.8 parts styrene/n-butylmethacrylate resin. The triboelectric charge on the toner after 10 minutes of roll milling was +48 uc/gram.

EXAMPLE IX

The procedure of Example VII was repeated with the exception that the toner composition was comprised of 0.4 parts of the quaternary salt telomer of Example II, 6 parts carbon black, and 9.36 parts styrene/n-butylmethacrylate resin. The triboelectric charge on the toner after 10 minutes of roll milling was +41 uc/gram.

EXAMPLE X

The procedure of Example VII was repeated with the exception that the toner composition was comprised of 0.8 parts of the quaternary salt telomer of Example II, 8 parts carbon black, and 91.2 parts styrene/n-butylmethacrylate resin. The tribo triboelectric charge on the toner after 10 minutes of roll milling was +46 uc/gram.

EXAMPLE XI

The procedure of Example VII was repeated with the exception that the toner composition was comprised of 0.4 parts of the quaternary salt telomer of Example II, 6 parts Regal 330 carbon black, and 93.6 parts of a styrene/butadiene resin, 90 percent by weight of styrene, 10 percent by weight of butadiene. The triboelectric charge on the toner after 10 minutes of roll milling was +32 uc/gram, as determined using a Faraday cage.

EXAMPLE XII

The procedure of Example VII was repeated with the exception that the toner composition which was comprised 3.2 parts of quaternary salt telomer of Example II, 6 parts Regal 330 carbon black, and 88.8 parts styrene/n-butylmethacrylate resin was prepared by solution blending the components, followed by solvent removal, and then attrition and classification to prepare toner particles. The triboelectric charge on the toner after 10 minutes of roll milling was +50 uc/gram.

Good quality prints of excellent resolution resulted when the developer composition of Examples VII, IX, X, XI and XII were tested in the same imaging fixture as used in Example VII.

A Faraday cage was employed to determine the triboelectric charge on the above toner compositions.

Other modifications of the present invention may occur to those skilled in the art upon a reading of the present disclosure and these are intended to be encompassed within the scope of the present invention.

What is claimed is:

1. A telomeric quaternary salt composition of the formula $$[A_xB_y]_Z$$

wherein A is styrene, and B is selected from a quaternized salt prepared from 2-vinylpyridine, 3-vinylpyridine, 4-vinylpyridine, and dimethylaminoethylmethacrylate, x and y are numbers representing mole fractions of A and B, the sum of x and y being equal to 1, and Z represents the degree of polymerization, wherein there results a polymeric quaternary salt having a number average molecular weight of from about 1,000 to about 10,000.

2. A composition in accordance with claim 1 wherein the telomeric quaternary salt is styrene/2-vinyl-N-butylpyridinium chloride monohydrate.

3. A composition in accordance with claim 1 wherein the telomeric quaternary salt is styrene/3-vinyl-N-butylpyridinium chloride monohydrate.

4. A composition in accordance with claim 1 wherein the telomeric quaternary salt is styrene/4-vinyl-N-butylpyridinium chloride monohydrate.

5. A compsition in accordance with claim 1 wherein the telomeric quaternary salt is styrene/2-vinyl-N-butylpyridinium bromide monohydrate.

6. A composition in accordance with claim 1 wherein the telomeric quaternary salt is styrene/3-vinyl-N-butylpyridinium bromide monohydrate.

7. A composition in accordance with claim 1 wherein the telomeric quaternary salt is styrene/4-vinyl-N-butylpyridinium bromide monohydrate.

8. A telomeric quaternary salt composition of the formula

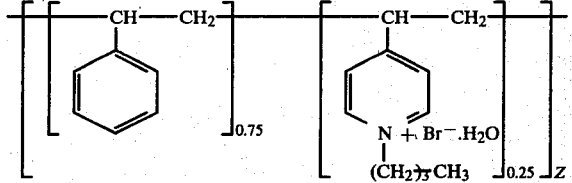

wherein Z represents the degree of polymerization thereby resulting in a telomeric quaternary salt having a number average molecular weight of 3,400 and a weight average molecular weight of 7,000.

* * * * *